United States Patent [19]

Maurer et al.

[11] 4,041,158
[45] Aug. 9, 1977

[54] O-ALKYL-O-[1-(3-NITROPHENYL)-2-CAR-BALKOXY-VINYL]-THIONO(THIOL)-PHOSPHORIC (PHOSPHONIC) ACID ESTERS

[75] Inventors: Fritz Maurer; Hans-Jochem Riebel, both of Wuppertal; Ingeborg Hammann, Cologne; Wilhelm Stendel, Wuppertal, all of Germany

[73] Assignee: Bayer Aktiengesellschaft, Leverkusen, Germany

[21] Appl. No.: 630,856

[22] Filed: Nov. 11, 1975

[30] Foreign Application Priority Data

Nov. 26, 1974 Germany .................. 2455763

[51] Int. Cl.$^2$ .................. A01N 9/36; C07F 9/18; C07F 9/205
[52] U.S. Cl. .................. 424/212; 260/941
[58] Field of Search .................. 260/941; 424/212

[56] References Cited

U.S. PATENT DOCUMENTS

| 2,894,018 | 7/1959 | Lorenz | 260/941 |
| 3,784,589 | 1/1974 | Large | 260/941 |

FOREIGN PATENT DOCUMENTS

| 1,035,392 | 7/1958 | Germany | 424/212 |

OTHER PUBLICATIONS

Derwent Japanese, vol. 1, No. 47 (1962) No. 18736/62.

*Primary Examiner*—Richard L. Raymond
*Attorney, Agent, or Firm*—Burgess, Dinklage & Sprung

[57] ABSTRACT

O-Alkyl-O-[1-(3-nitrophenyl)-2-carbalkoxy-vinyl]-thiono(thiol)-phosphoric (phosphonic) acid esters of the formula (I)

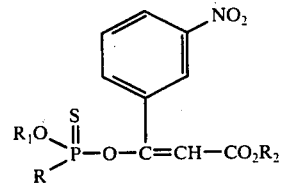

in which
R is alkyl, alkoxy or alkylthio, each with 1 to 6 carbon atoms, or phenyl, and
$R_1$ and $R_2$ each independently is alkyl with 1 to 6 carbon atoms,
which possess insecticidal properties.

10 Claims, No Drawings

O-ALKYL-O-[1-(3-NITROPHENYL)-2-CARBALKOXY-VINYL]-THIONO(THIOL)-PHOSPHORIC (PHOSPHONIC) ACID ESTERS

The present invention relates to and has for its objects the provision of particular new O-alkyl-O-[1-(3-nitrophenyl)-2-carbalkoxy-vinyl]-thiono(thiol)-phosphoric (phosphonic) acid esters which possess insecticidal properties, active compositions in the form of mixtures of such compounds with solid and liquid dispersible carrier vehicles, and methods for producing such compounds and for using such compounds in a new way especially for combating pests, e.g. insects, with other and further objects becoming apparent from a study of the within specification and accompanying examples.

It is known from published Japanese Patent Application No. 18,736/62 that O-vinylthionophosphoric acid esters, for example O,O-dimethyl- (Compound A) and O,O-diethyl-O-[1-(4-nitrophenyl)-2-carbethoxyvinyl]-thionophosphoric acid ester (Compound B), possess insecticidal and acaricidal properties.

The present invention relates O-vinylthiono (thiol) phosphoric (phosphonic) acid esters of the formula

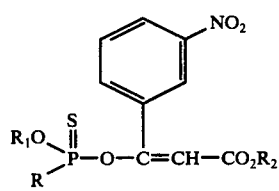
(I)

in which
R is alkyl, alkoxy or alkylthio, each with 1 to 6 carbon atoms, or phenyl, and
$R_1$ and $R_2$ each independently is alkyl with 1 to 6 carbon atoms.

The general formula (I) includes the corresponding cis- and trans-isomers of structure (II) and (III) and mixtures of these components:

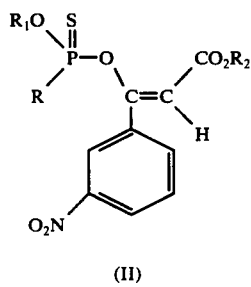 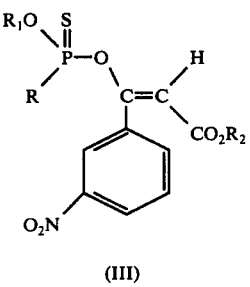

(II)              (III)

Preferably, R is straight-chain or branched alkyl with 1 to 3, especially 1 or 2, carbon atoms, or straight-chain or branched alkoxy or alkylthio with 1 to 4, especially 1 to 3, carbon atoms, or phenyl, and $R_1$ and $R_2$ which may be the same or different, are straight-chain or branched alkyl with 1 to 4, especially 1 to 3, carbon atoms.

Surprisingly, the O-vinylthiono(thiol)phosphoric(phosphonic)acid esters according to the invention have a better insecticidal action and a lower toxicity towards warm-blooded animals than the previously known compounds of analogous structure and of the same type of action. They are not only active in the field of plant protection but also in the hygiene field, the field of protection of stored products and the veterinary field. The compounds according to the invention thus represent a genuine enrichment of the art.

The invention also provides a process for the preparation of an O-vinylthiono(thiol)phosphoric(phosphonic) acid ester of the formula (I) in which a thiono(thiol)-phosphoric(phosphonic) acid ester halide of the general formula

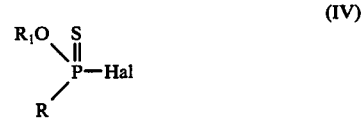
(IV)

in which
R and $R_1$ have the abovementioned meanings and
Hal is halogen, preferably chlorine,
is reacted with a 3-nitrobenzoylacetic acid alkyl ester of the general formula

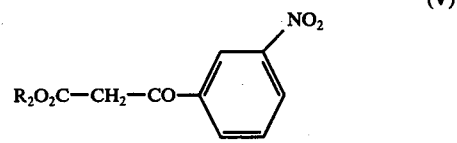
(V)

or the corresponding enol compound of the general formula

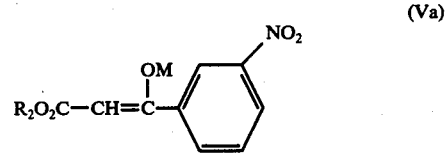
(Va)

in which
$R_2$ has the abovementioned meaning and
M is one equivalent of an alkali metal or alkaline earth metal or ammonium.

The reaction may be carried out in the presence of an acid acceptor, and it may be carried out in the presence of a solvent.

If, for example, O-ethyl-O-iso-propyl-thionophosphoric acid diester chloride and 3-nitrobenzoylacetic acid n-butyl ester are used as starting materials, the course of the reaction can be represented by the following formula scheme:

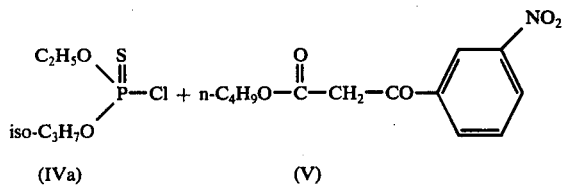

(IVa)        (V)

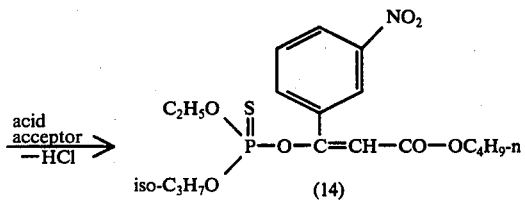

(14)

The thiono(thiol)phosphoric(phosphonic) acid ester halides (IV) to be used as starting materials are known from the literature and can be prepared in accordance with generally customary processes, as can the 3-nitrobenzoylacetic acid alkyl esters or enols (V and Va) (see French Patent No. 1,318,368). The following may be mentioned individually as examples of these compounds: O,O-dimethyl-, O,O-diethyl-, O,O-di-n-propyl-, O,O-di-iso-propyl-, O,O-di-n-butyl-, O,O-di-iso-butyl-, O,O-di-sec.-butyl-, O,O-di-tert.-butyl-, O-ethyl-O-n-propyl-, O-ethyl-O-iso-propyl-, O-n-butyl-O-ethyl-, O-ethyl-O-sec.-butyl- and O-ethyl-O-methylthionophosphoric acid diester chloride, as well as O,S-dimethyl-, OS-diethyl-, O,S-di-n-propyl-, O,S-di-isopropyl-, O,S-di-n-butyl, O,S-di-iso-butyl-, O,S-di-tert.-butyl-, O-ethyl-S-n-propyl-, O-ethyl-S-iso-propyl-, O-ethyl-S-n-butyl-, O-ethyl-S-sec.-butyl-, O-n-propyl-S-ethyl-, O-n-propyl-S-iso-propyl-, O-n-butyl-S-n-propyl- and O-sec.-butyl-S-ethylthionothiolphosphoric acid diester chloride, and also O-methyl-, O-ethyl-, O-n-propyl-, O-iso-propyl-, O-n-butyl-, O-sec.-butyl-, O-iso-butyl- and O-tert.-butyl-methane-, -ethane-, -n-propane-, -iso-propane- and -benzene-thionophosphonic acid ester chloride, as well as 3-nitrobenzoylacetic acid methyl ester, ethyl ester, n-propyl ester, iso-propyl ester, n-butyl ester, iso-butyl ester or sec.-butyl ester.

The reaction according to the invention is preferably carried out in the presence of a solvent which term includes a mere diluent. Practically all inert organic solvents can be used for this purpose. These include, in particular, aliphatic and aromatic, optionally chlorinated, hydrocarbons, for example benzene, toluene, xylene, benzine, methylene chloride, chloroform, carbon tetrachloride or chlorobenzene; ethers, for example diethyl ether, dibutyl ether and dioxane; ketones, for example acetone, methyl ethyl ketone, methyl isopropyl ketone and methyl isobutyl ketone; and nitriles, for example acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate, ethylate and tert.-butylate, have proved particularly suitable, as have aliphatic, aromatic or heterocyclic amines, for example triethylamine, trimethylamine, dimethylaniline, dimethylbenzylamine and pyridine.

The reaction temperature can be varied within a wide range. In general, the reaction is carried out at 0° to 120° C, preferably at 20° to 80° C.

The reaction is in general allowed to take place under normal pressure.

To carry out the process, the components are in most cases employed in equimolar amounts; the 3-nitrobenzoylacetic acid alkyl ester is optionally employed in 10-20% excess. The reaction is preferably carried out in the presence of one of the abovementioned solvents, if appropriate in the presence of an acid acceptor, at the stated temperatures. After a reaction time of from one to several hours, in most cases at elevated temperatures, the reaction mixture may be cooled and poured into an organic solvent, for example toluene, and the organic phase separated off. The latter may be washed with 5% strength sodium hydroxide solution and then with water, and may be dried, and the solvent may be distilled off.

The new compounds are obtained in the form of oils, many of which can not be distilled without decomposition, but they may be freed from the last volatile constituents by so-called "slight distillation", that is to say by prolonged heating under reduced pressure to moderately elevated temperatures, and they may be purified in this way. They are characterized by the refractive index.

As has already been mentioned, the O-vinylthiono(-thiol) phosphoric(phosphonic) acid esters according to the invention are distinguished by an excellent insecticidal activity. They are not only active against plant pests, hygiene pests and pests of stored products, but also, in the veterinary medicine field, against animal parasites (ectoparasites), such as parasitic fly larvae. They combine a low phytotoxicity and low toxicity to warm-blooded animals with a good action against both sucking and biting insects.

For this reason, the compounds according to the invention can be employed successfully as pesticides in plant protection and in the hygiene field, the field of protection of stored products and the veterinary field.

The active compounds of the invention are well-tolerated by plants, have a favorable level of toxicity to warm-blooded animals and can be used for combating all or individual stages of development, including the pre-embryonic, normally sensitive and resistant stages of development, of arthropods/nematodes/plant-pathogenic fungi, where these are known as pests or pathogens of plant diseases in agriculture, in forestry, in the protection of stored products and of materials, and in hygiene.

the economically important pests in agriculture and forestry, as well as pests of stored products, material pests and hygiene pests, include: from the order of the Isopoda, for example, *Oniscus asellus, Armadillidium vulgare* and *Porcellio scaber;* from the order of the Diplopoda, for example, *Blaniulus guttulatus;* from the order of the Chilopoda, for example, *Geophilus carpophagus* and *Scutigera* spec.; from the order of the Symphyla, for example, *Scutigerella immaculata;* from the order of the Arachnida, for example *Scorpio maurus* and *Latrodectus mactans;* from the order of the Acarina, for example, *Acarus siro, Argas reflexus, Ornithodoros moubata, Dermanyssus gallinae, Eriophyes ribis, Phyllocoptruta oleivora, Boophilus microplus, Rhipicerhalus evertsi, Sarcoptes scabiei,* Tarsonemus spec., *Bryobia praetiosa, Panonychus citri, Panonychus ulmi, Tetranychus telarius, Tetranychus tumidus* and *Tetranychus urticae;* from the order of the Thysanura, for example, *Lepisma saccharina;* from the order of the Collembola, for example, *Onychiurus armatus;* from the order of the Orthoptera, for example, *Blatta orientalis, Periplaneta americana, Leucophaea maderae, Blattella germanica, Acheta domesticus,* Gryllotalpa spec., *Locusta migroteria migratorioides; Melanoplus differentialis* and *Schistocerca gregaria;* from the order of the Dermaptera, for example, *Forficula auricularia;* from the order of the Isoptera, for example Reticulitermes spec.; from the order of the Anoplura, for example, *Phylloxera vastatrix,* Pemphigus spec. and *Pediculus humanus corporis;* from the order of the Thysanoptera, for example, *Hercinothrips femoralis* and *Thrips tabaci;* from the order of the Heteroptera, for example, Eurygaster spec., *Dysdercus intermedius, Piesma quadrata, Cimex lectularius, Rhodnius prolixus* and Triatoma spec.; from the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,*

*Myzus cerasi, Myzus persicae, Phorodon humuli, Rhopalosiphum padi,* Empoasca spec., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spec. and Psylla spec.; from the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spec., *bucculatrix thurberiella, Phyllocnistis citrella,* Agrotis spec., Euxoa spec., Feltia spec., *Earias insulana,* Heliothis spec., *Laphygma exigua, Mamestra brassicae, Panolis flammea, Prodenia litura,* Spodoptera spec., *Trichoplusia ni, Carpocapsa pomonella,* Pieris spec., Chilo spec., *Pyrausta nubilalis, Ephestia kuhniella, Galleria mellonella, Cacoecia podana, Capua reticulana, Choristoneura fumiferana, Clysia ambiguella, Homona magnanima* and *Tortrix viridana;* from the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spec., *Psylliodes chrysocephala, Epilachna varivestis,* Atomaria spec., *Oryzaephilus surinamensis,* Anthonomus spec., Sitophilus spec., *Otiorrhynchus sulcatus, Cosmopolites sordidus, Ceuthorrhynchus assimilis, Hypera postica,* Dermestes spec., Trogoderma spec., Anthrenus spec., Attagenus spec., Lyctus spec., *Meligethes aeneus,* Ptinus spec., *Niptus hololeucus, Gibbium pyslloides,* Tribolium spec., *Tenebrio molitor, Agriotes spec., Conoderus spec., Melolontha melolontha, Amphimallus solstitialis* and *costelytra zealandica;* from the order of the Hymenoptera, for example, Diprion spec., Hoplocampa spec., Lasius spec., *Monomorium pharaonis* and Vespa spec.; from the order of the Diptera, for example, Aedes spec., Anopheles spec., Culex spec., *Drosophila melanogaster, Musca domestica,* Fannia spec., *Stomoxys calcitrans,* Hypoderma spec., *Bibio hortulanus,* Oscinella frit, Phorbia spec., *Pegomyia hyoscyami, Calliphora erythrocephala,* Lucilia spec., Chrysomyia spec., *Ceratitis capitata, Dacus oleae* and *Tipula paludosa;* and from the order of the Siphonaptera, for example, *Xenopsylla cheopis.*

When used against hygiene pests and pests of stored products, the active compounds are distinguished by an excellent residual action on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arlypolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, or acaricides, nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50-100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20-100% by weight of the acitve compound.

Furthermore, the present invention contemplates methods of selectively killing, combating or controlling pests, e.g. insects, which comprises applying to at least one of correspondingly (a) such insects, and (b) the corresponding habitat thereof, i.e. the locus to be protected, e.g. to a growing crop, to an area where a crop is to be grown or to a domestic animal, a correspondingly combative or toxic amount, i.e. an insecticidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples.

EXAMPLE 1

Drosophila test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 cm³ of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% means that all the flies were killed; 0% means that no flies were killed.

The active compounds, the concentrations of the active compounds, the evaluation times and the results can be seen from the following Table 1:

Table 1

| Active compound | Active compound concentration in % by weight | Degree of destruction in % after 1 day |
|---|---|---|
| NO₂—⟨⟩—C(OP(S)(OCH₃)₂)=CH—CO—OC₂H₅ (known) (A) | 0.01<br>0.001 | 100<br>0 |
| ⟨NO₂⟩—C(OP(S)(OC₂H₅)₂)=CH—CO—OC₂H₅ (1) | 0.01<br>0.001 | 100<br>99 |
| ⟨NO₂⟩—C(OP(S)(OC₂H₅)₂)=CH—CO—OC₃H₇-iso (8) | 0.01<br>0.001 | 100<br>100 |
| ⟨NO₂⟩—C(OP(S)(OC₂H₅)(OC₃H₇-n))=CH—CO—OCH(CH₃)₂ (9) | 0.01<br>0.001 | 100<br>98 |

EXAMPLE 2

Laphygma test

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cotton leaves (*Gossypium hirsutum*) were sprayed with the preparation of the active compound until dew-moist and were then infested with caterpillars of the owlet moth (*Laphygma exigua*).

After the specified periods of time, the destruction in % was determined. 100% means that all caterpillars had been killed whilst 0% indicates that no caterpillars had been killed.

The active compounds, the concentrations of the active compound, the evaulation times and the results can be seen from the following Table 2:

Table 2

| Active compound | Active compound concentration in % by weight | Degree of destruction in % after 3 days |
|---|---|---|
| NO₂—⟨⟩—C(OP(S)(OCH₃)₂)=CH—CO—OC₂H₅ (known) (A) | 0.01<br>0.001 | 100<br>0 |

Table 2-continued
(Laphygma test)

| Active compound | Active compound concentration in % by weight | Degree of destruction in % after 3 days |
|---|---|---|
| 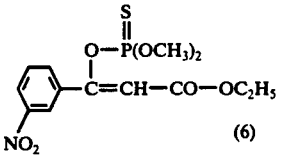 (6) | 0.01<br>0.001 | 100<br>85 |
| 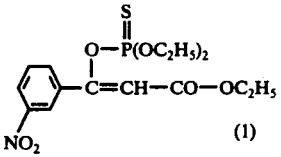 (1) | 0.01<br>0.001 | 100<br>100 |
| | 0.01<br>0.001 | 100<br>100 |
|  (3) | | |
| 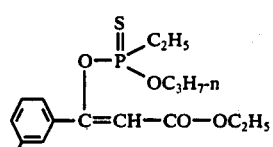 (2) | 0.01<br>0.001 | 100<br>75 |
| 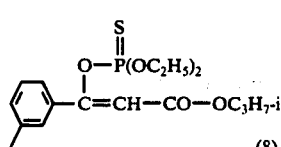 (8) | 0.01<br>0.001 | 100<br>100 |

EXAMPLE 3

Phaedon larvae test (long-term action after spraying)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*), which were about 10–15 cm high, were sprayed with the preparation of the active compound until dripping wet.

After the specified periods of time, the plants were infested with mustard beetle larvae (*Phaedon cochleariae*). After intervals of 3 days, the destruction in % was determined. 100% means that all beetle larvae had been killed whereas 0% means that none of the beetle larvae had been killed.

The active compounds, the concentrations of the active compounds, the evaluation times and the results can be seen from Table 3 which follows:

Table 3

Long-term action after spraying/0.05% of active compound
(Phaedon larvae on *Brassica oleracea*)

| Active compound | % destruction after | | | | |
|---|---|---|---|---|---|
| | 4 | 8 | 11 | 15 | 18 days |
| 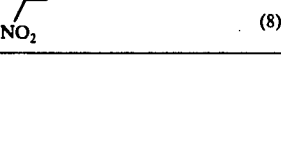 (known) (B) | 100 | 100 | 50 | 0 | |
| 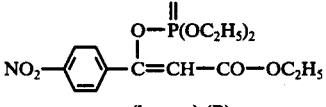 (10) | 100 | 100 | 100 | 100 | 90 |
| 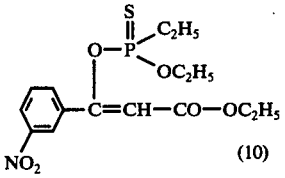 (2) | 100 | 100 | 100 | 100 | 100 |

EXAMPLE 4

Myzus test (long-term action after spraying)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*), which were about 10–15 cm high, were sprayed with the preparation of the active compound until dripping wet.

After the specified periods of time, the plants were infested with aphids (*Myzus persicae*). After intervals of 3 days, the destruction in % was determined. 100% means that all aphids had been killed whereas 0% means that none of the aphids had been killed.

The active compounds, the concentrations of the active compounds, the evaluation time and the results can be seen from Table 4 which follows:

Table 4

Long-term action after spraying/0.05% of active compund
(*Myzus persicae* on *Brassica oleracea*)

| Active compound | % destruction after | | | |
|---|---|---|---|---|
| | 4 | 8 | 11 | 15 days |
| NO₂—⟨phenyl⟩—C(O—P(S)(OC₂H₅)₂)=CH—CO—OC₂H₅ (known) (B) | 50 | 0 | | |
| NO₂—⟨phenyl⟩—C(O—P(S)(C₂H₅)(OC₂H₅))=CH—CO—OC₂H₅ (10) | 100 | 70 | 45 | 50 |
| NO₂—⟨phenyl⟩—C(O—P(S)(C₂H₅)(OC₃H₇-n))=CH—CO—OC₂H₅ (2) | 100 | 100 | 95 | 100 |

EXAMPLE 5

Toxicity test/peroral

Test animal: Albino rat (*Rattus norvegicus*)
Evaluation after: 7 days

To produce a suitable preparation of active compound, 3 parts by weight of active compound were mixed with 2.8 parts by weight of highly-dispersed silica and 4.2 parts by weight of talc. Suspensions which contain, in 1 ml of liquid, the amount of active compound to be applied per 100 g of animal weight, were prepared from the above active compound concentrate, with a little added powdered vegetable gum, by grinding with water. Dosing was effected volumetrically after weighing the test animals. A steel knob-ended probe was used for oral administration. The evaluation was carried out in each case after the end of the above-mentioned time interval, calculated from the administration of the active compound.

The LD$_{50}$ values (dose of active compound at which 50% of the treated animals were killed) were determined in the usual manner from the mortality figures of the doses, which were varied in geometrical progression.

The active compounds and LD$_{50}$ values can be seen from the Table 5 which follows:

Table 5

Toxicity test (albino rat/peroral)

| Active compound | LD$_{50}$ values (in mg/kg of body weight) |
|---|---|
| NO₂—⟨phenyl⟩—C(O—P(S)(OC₂H₅)₂)=CH—CO—OC₂H₅ (known) (B) | 10-25 |
| NO₂—⟨phenyl⟩—C(O—P(S)(OC₂H₅)(SC₃H₇-n))=CH—CO—OC₂H₅ (7) | 100-250 |
| NO₂—⟨phenyl⟩—C(O—P(S)(OC₂H₅)(OC₃H₇-n))=CH—CO—OC₂H₅ (4) | 50-100 |
| NO₂—⟨phenyl⟩—C(O—P(S)(OC₂H₅)(phenyl))=CH—CO—OC₂H₅ (5) | 50-100 |

EXAMPLE 6

Test with parasitic fly larvae

Solvent: 35 parts by weight of ethylene polyglycol monomethyl ether
35 parts by weight of nonylphenol polyglycol ether To produce a suitable preparation of active compound, 30 parts by weight of the active substance in question were mixed with the stated amount of solvent which contained the abovementioned proportion of emulsifier and the concentrate thus obtained was diluted with water to the desired concentration.

About 20 fly larvae (*Lucilia cuprina*) were introduced into a test tube which contains approximately 2 cm³ of horse muscle. 0.5 ml of the preparation of active compound was applied to this horse meat. After 24 hours, the degree of destruction in % was determined. 100% means that all larvae had been killed and 0% means that no larvae had been killed.

The active compounds investigated, the concentrations of the active compounds used and the results obtained can be seen from Table 6 which follows:

Table 6

(Test with parasitic fly larvae)

| Active compound | Active compound concentration in ppm | Degree of destruction in % (*Lucilla cuprina* res.) |
|---|---|---|
| (structure 7) | 100<br>30<br>10 | 100<br>100<br>100 |
| (known) (B) | 100<br>10<br>0 | 100<br>>50<br>0 |

18.8 g (0.1 mole) of O,O-diethylthionophosphoric acid diester chloride were added dropwise to a suspension of 26 g (0.11 mole) of 3-nitrobenzoylacetic acid ethyl ester and 15.2 g (0.11 mole) of potassium carbonate in 200 ml of acetonitrile at room temperature. The reaction mixture was then warmed to 60°–70° C for 6 hours, cooled and poured into 300 ml of toluene. The toluene phase was washed twice with 150 ml of 5% strength sodium hydroxide solution at a time and once with 300 ml of water, dried over sodium sulfate and then concentrated. It was then subjectd to slight distillation. 35 g (90% of theory) of O,O-diethyl-O-[1-(3-nitrophenyl)-2-carbethoxy-vinyl]-thionophosphoric acid ester were obtained as a brown oil of refractive index $n_D^{21}$: 1.5394.

The following compounds of the formula

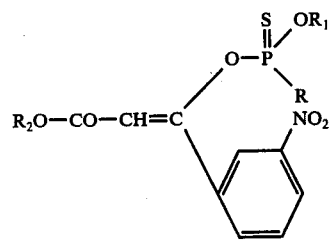

were prepared analogously:

The following further examples are set forth to illustrate, without limitation, the manner of producing the instant compounds according to the present invention:

EXAMPLE 7

(1)

| Example No. | $R_2$ | $R_1$ | R | Yield (% of theory) | Refractive index |
|---|---|---|---|---|---|
| 2 | —$C_2H_5$ | —$C_3H_7$-n | —$C_2H_5$ | 81 | $n_D^{21}$: 1.5491 |
| 3 | —$C_2H_5$ | —$C_3H_7$-iso | —$CH_3$ | 75 | $n_D^{24}$: 1.5480 |
| 4 | —$C_2H_5$ | —$C_2H_5$ | —$OC_3H_7$-n | 79 | $n_D^{23}$: 1.5382 |

-continued

| Example No. | $R_2$ | $R_1$ | R | Yield (% of theory) | Refractive index |
|---|---|---|---|---|---|
| 5 | —$C_2H_5$ | —$C_2H_5$ | (phenyl) | 64 | $n_D^{23}$: 1.5851 |
| 6 | —$C_2H_5$ | —$CH_3$ | —$OCH_3$ | 64 | $n_D^{23}$: 1.5417 |
| 7 | —$C_2H_5$ | —$C_2H_5$ | —$SC_3H_7$-n | 48 | $n_D^{23}$: 1.5582 |
| 8 | —$C_3H_7$-iso | —$C_2H_5$ | —$OC_2H_5$ | 85 | $n_D^{23}$: 1.5285 |
| 9 | —$C_3H_7$-iso | —$C_2H_5$ | —$OC_3H_7$-n | 88 | $n_D^{23}$: 1.5253 |
| 10 | —$C_2H_5$ | —$C_2H_5$ | —$C_2H_5$ | 66 | $n_D^{20}$: 1.5410 |

Other compounds which can similarly be prepared include:

| Compound No. | $R_2$ | $R_1$ | R |
|---|---|---|---|
| 11 | —$CH_3$ | —$C_4H_9$-n | —$C_3H_7$-n |
| 12 | —$C_3H_7$-n | —$C_2H_5$ | —$SC_2H_5$ |
| 13 | —$C_4H_9$-t | —$C_2H_5$ | —$SCH_3$ | and the like.

It will be appreciated that the instant specification and examples are set forth by way of illustration and not limitation, and that various modifications and changes may be made without departing from the spirit and scope of the present invention.

What is claimed is:

1. An O-alkyl-O-[1-(3-nitrophenyl)-2-carbalkoxyvinyl]-thiono(thiol)-phosphoric(phosphonic) acid ester of the formula

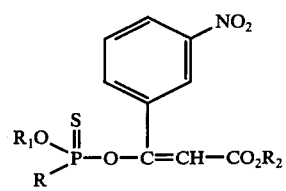

in which
R is alkyl, alkoxy or alkylthio, each with 1 to 6 carbon atoms, or phenyl, and
$R_1$ and $R_2$ each independently is alkyl with 1 to 6 carbon atoms.

2. A compound according to claim 1 in which R is alkyl with 1 to 3 carbon atoms, or alkoxy or alkylthio with 1 to 4 carbon atoms, or phenyl, and $R_1$ and $R_2$ each is alkyl with 1 to 4 carbon atoms.

3. A compound according to claim 1 wherein such compound is O,O-diethyl-O-[1-(3-nitrophenyl)-2-carbethoxyvinyl]-thionophosphoric acid ester of the formula

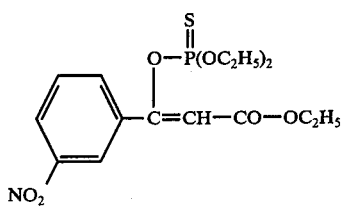

4. A compound according to claim 1 wherein such compound is O-isopropyl-O-[1-(3-nitrophenyl)-2-carbethoxyvinyl]-methanethionophosphonic acid ester of the formula

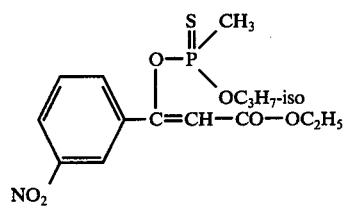

5. A compound according to claim 1 wherein such compound is O,O-dimethyl-O-[1-(3-nitrophenyl)-2-carbethoxyvinyl]-thionophosphoric acid ester of the formula

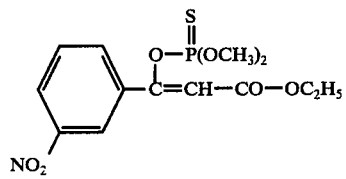

6. A compound according to claim 1 wherein such compound is O,O-diethyl-O-[1-(3-nitrophenyl)-2-carbisopropoxy-vinyl]-thionophosphoric acid ester of the formula

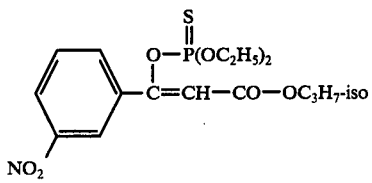

7. A compound according to claim 1 wherein such compound is O-ethyl-O-n-propyl-O-[1-(3-nitrophenyl)-2-carbisopropoxy-vinyl]-thionophophoric acid ester of the formula

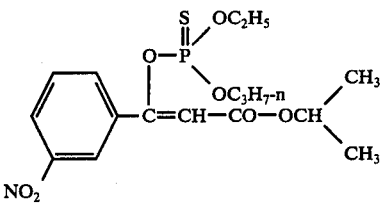

8. An insecticidal composition containing as active ingredient an insecticidally effective amount of a compound according to claim 1 in admixture with a diluent.

9. A method of combating insect pests which comprises applying to the pests or a habitat thereof an insecticidally effective amount of a compound according to claim 1.

10. The method according to claim 9 in which said compound is

O,O-diethyl-O-[1-(3-nitrophenyl)-2-carbethoxyvinyl]-thionophosphoric acid ester, O-isopropyl-O-[1-(3-nitrophenyl)-2-carbethoxyvinyl]-methanethionophosphonic acid ester, O,O-dimethyl-O-[1-(3-nitrophenyl)-2-carbethoxyvinyl]-thionophosphoric acid ester, O,O-diethyl-O-[1-(3-nitrophenyl)-2-carbisopropoxyvinyl]-thionophosphoric acid ester, or O-ethyl-O-n-propyl-O-[1-(3-nitrophenyl)-2-carbisopropoxy-vinyl]-thionophosphoric acid ester.

* * * * *